United States Patent [19]

Irikura et al.

[11] 4,398,029

[45] Aug. 9, 1983

[54] QUINOLINE CARBOXYLIC ACID DERIVATIVES AND PROCESS FOR THE PREPARATION

[75] Inventors: Tsutomu Irikura, Oizumigakuen; Hiroshi Koga, Omiya; Satoshi Murayama, Nogi, all of Japan

[73] Assignee: Kyorin Seiyaku Kabushiki Kaisha, Tokyo, Japan

[21] Appl. No.: 236,168

[22] Filed: Feb. 20, 1981

[51] Int. Cl.$^3$ .................. C07D 401/04; A61K 31/47; A61K 31/535; C07D 413/04
[52] U.S. Cl. .................. 544/363; 424/245; 424/248.53; 424/25 D; 424/258; 544/4; 544/128; 544/336; 546/8; 546/156
[58] Field of Search ........................................ 544/363

[56] References Cited

U.S. PATENT DOCUMENTS

| | | | |
|---|---|---|---|
| 3,849,421 | 11/1974 | Nakagome et al. | 546/123 |
| 4,017,622 | 4/1977 | Minami et al. | 544/363 |
| 4,146,719 | 3/1979 | Irikura | 544/363 |

FOREIGN PATENT DOCUMENTS

| | | | |
|---|---|---|---|
| 2939786 | 4/1980 | Fed. Rep. of Germany | 544/363 |
| 56-128764 | 10/1981 | Japan | 544/363 |

*Primary Examiner*—Donald G. Daus
*Assistant Examiner*—James H. Turnipseed
*Attorney, Agent, or Firm*—Toren, McGeady and Stanger

[57] ABSTRACT

This invention relates to new compounds of value as antibacterial agent. More particularly, it relates to quinoline carboxylic acid derivatives, the hydrates and the salts thereof.

3 Claims, No Drawings

QUINOLINE CARBOXYLIC ACID DERIVATIVES AND PROCESS FOR THE PREPARATION

FIELD OF THE INVENTION

This invention relates to new and useful quinoline carboxylic acid derivatives having potent antibacterial activities. Antibacterial agent's such as nalidixic acid, piromidic acid, and pipemidic acid have been proved highly effective in the therapy of infections due to gram-negative bacteria, but such agents suffer from the serious disadvantage of having only weak activities against most gram-positive bacteria and *Pseudomonas aeruginosa*.

It is therefore an object of this invention to provide a novel antibacterial agent and a novel preparation process therefore.

The compounds of the present invention are particularly useful in that they possess potent antibacterial activity against both Gram-positive and Gram-negative bacteria, including *Pseudomonas aeruginosa*.

SUMMARY OF THE INVENTION

The present invention is to provide new compounds as defined below and their production processes
6,8-difluoro-1,4-dihydro-1-methyl-4-oxo-7-(1-piperazinyl)-quinoline-3-carboxylic acid (I),
6,8-difluoro-1,4-dihydro-4-oxo-7-(1-piperazinyl)-1-n-propylquinoline-3-carboxylic acid (II),
1-allyl-6,8-difluoro-1,4-dihydro-4-oxo-7-(1-piperazinyl)-quinoline-3-carboxylic acid (III),
6,8-difluoro-1-(2-fluoroethyl)-1,4-dihydro-4-oxo-7-(1-piperazinyl)-quinoline-3-carboxylic acid (IV),
6,8-difluoro-1-(2-fluoroethyl)-1,4-dihydro-7-(4-methyl-1-piperazinyl)-4-oxoquinoline-3-carboxylic acid (V),
7-(4-allyl-1-piperazinyl)-1-ethyl-6,8-difluoro-1,4-dihydro-4-oxoquinoline-3-carboxylic acid (VI),
1-ethyl-7-(4-ethyl-1-piperazinyl)-6,8-difluoro-1,4-dihydro-4-oxoquinoline-3-carboxylic acid (VII),
1-ethyl-6,8-difluoro-1,4-dihydro-7-[4-(2-hydroxyethyl)-1-piperazinyl]-4-oxoquinoline-3-carboxylic acid (VIII),
1-ethyl-6,8-difluoro-1,4-dihydro-7-(4-hydroxy-1-piperidinyl)-4-oxoquinoline-3-carboxylic acid (IX),
1-ethyl-6,8-difluoro-1,4-dihydro-7-(3-hydroxy-1-piperidinyl)-4-oxoquinoline-3-carboxylic acid (X),
1-ethyl-6,8-difluoro-1,4-dihydro-4-oxo-7-(1-pyrrolidinyl)-quinoline-3-carboxylic acid (XI),
1-ethyl-6,8-difluoro-1,4-dihydro-7-(4-morpholinyl)-4-oxoquinoline-3-carboxylic acid (XII),
1-ethyl-6,8-difluoro-1,4-dihydro-7-(4-dimethylamino-1-piperidinyl)-4-oxoquinoline-3-carboxylic acid (XIII),
6,8-difluoro-1,4-dihydro-1-(2-hydroxyethyl)-4-oxo-7-(1-piperazinyl)-quinoline-3-carboxylic acid (XIV),
6,8-difluoro-1,4-dihydro-4-oxo-7-(1-piperazinyl)-1-vinylquinoline-3-carboxylic acid (XV),
and the hydrates and the pharmaceutically acceptable salts of these compounds.

The compounds of the present invention are prepared by the following methods.

The compounds (I–V, IX–XIII, and XIV) are prepared by the reaction of a compound of the formula (XVI)

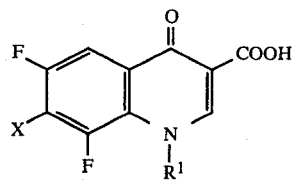

wherein $R^1$ is methyl, ethyl, n-propyl, allyl, 2-fluoroethyl, or 2-hydroxyethyl group and X is halogen, with piperazine, N-methyl-piperazine, 3-hydroxypiperidine, pyrrolidine, morpholine, 4-dimethylaminopiperidine, or 4-hydroxypiperidine, in an inert solvent such as, for example, water, alcohols, pyridine, picoline, N,N-dimethylformamide, dimethylsulfoxide, or the like, or in the absence of a solvent, at a temperature in the range of 60° C. to 180° C.

The compounds (VI–VIII) are prepared by the treatment of 1-ethyl-6,8-difluoro-1,4-dihydro-4-oxo-7-(1-piperazinyl)quinoline-3-carboxylic acid or the salts, with allyl halide, ethyl halide, or 2-hydroxyethyl halide. The reaction is accomplished within several hours by heating in the range of room temperature to 150° C. in an inert solvent such as, for example, water, alcohols, pyridine, picoline, N,N-dimethylformamide, dimethylsulfoxide, or the like, or in the absence of a solvent, in the presence of a base, as a dehydrohalogenating agent, such as alkali hydroxide, alkali carbonate, or amines.

The compound (XV) is obtained by the alkaline treatment of 7-(4-acetyl-1-piperazinyl)-1-(2-chloroethyl)-6,8-difluoro-1,4-dihydro-4-oxoquinoline-3-carboxylic acid ethyl ester.

The salts, such as, for example, sodium, potassium, calcium, magnesium, aluminum, ceric, chromic, cobaltic, cupric, ferric, silver, zinc, and organic base salts or hydrochlorides, sulfates, phosphates, acetates, lactates, and methanesulfonates, or the like, of the compounds of the present invention are obtained by the usual manner.

DETAILED DESCRIPTION OF THE INVENTION

The following examples serve to illustrate the invention.

EXAMPLE 1

6,8-Difluoro-1,4-dihydro-1-methyl-4-oxo-7-(1-piperazinyl)quinoline-3-carboxylic acid hydrochloride A mixture of 6,7,8-trifluoro-1,4-dihydro-1-methyl-4-oxo-quinoline-3-carboxylic acid (0.22 g), piperazine (0.37 g), and pyridine (3 ml) was refluxed for 4 hours. The reaction mixture was evaporated to dryness. The residue was acidified by the addition of hot aqueous acetic acid solution and the insoluble materials were removed by filtration. The filtrate was adjusted to pH 1 with concentrated hydrochloric acid and cooled. The resulting precipitate was filtered off and recrystallized from water to give 6,8-difluoro-1,4-dihydro-1-methyl-4-oxo-7-(1-piperazinyl)quinoline-3-carboxylic acid hydrochloride (0.13 g), mp 286°–288° C. (decomp.).

|  | C | H | N |
| --- | --- | --- | --- |
| Anal. Calcd. for $C_{15}H_{15}F_2N_3O_3 \cdot HCl$: | 50.08 | 4.48 | 11.68 |
| Found: | 49.98 | 4.38 | 11.58 |

The starting material, 6,7,8-trifluoro-1,4-dihydro-1-methyl-4-oxoquinoline-3-carboxylic acid, was obtained by the following method.

A mixture of 6,7,8-trifluoro-1,4-dihydro-4-oxoquinoline-3-carboxylic acid ethyl ester (0.3 g), anhydrous potassium carbonate (0.8 g), methyl iodide (1.6 g), and N,N-dimethyl-formamide (DMF) (10 ml) was heated with stirring at 90°–100° C. for 10 hours. The mixture was evaporated to dryness. The residue was treated with water, extracted with dichloromethane. The organic layer was washed with water, dried over anhydrous sodium sulfate, and evaporated. The residue was added to a mixture of 18% hydrochloric acid (5 ml) and ethanol (2.5 ml) and the mixture was refluxed for 2.5 hours. After water (5 ml) and ethanol (5 ml) added and cooled, the resulting precipitate was filtered off and recrystallized from a mixture of DMF and ethanol to give 6,7,8-trifluoro-1,4-dihydro-1-methyl-4-oxoquinoline-3-carboxylic acid (0.22 g), mp 255°–258° C.

EXAMPLE 2

6,8-Difluoro-1,4-dihydro-4-oxo-7-(1-piperazinyl)-1-n-propylquinoline-3-carboxylic acid hydrochloride A mixture of 6,7,8-trifluoro-1,4-dihydro-4-oxo-1-n-propyl-quinoline-3-carboxylic acid (0.22 g), piperazine )0.34 g), and pyridine (3 ml) was refluxed for 6 hours. The mixture was evaporated to dryness, adjusted to pH 1 with aqueous hydrochloric acid solution, and cooled. The solid was filtered off and recrystallized from water to afford 6,8-difluoro-1,4-dihydro-4-oxo-7-(1-piperazinyl)-1-n-propylquinoline-3-carboxylic acid hydrochloride (0.11 g), mp 279°–282° C. (decomp.).

|  | C | H | N |
|---|---|---|---|
| Anal. Calcd. for $C_{17}H_{19}F_2N_3O_3HCl$: | 52.65 | 5.20 | 10.83 |
| Found: | 52.46 | 5.16 | 10.68 |

The preparation of the starting material, 6,7,8-trifluoro-1,4-dihydro-4-oxo-1-n-propylquinoline-3-carboxylic acid (mp 202°–205° C.), and accomplished by the same method as described for that of the starting material in Example 1 by using n-propyl-bromide in place of methyl iodide.

EXAMPLE 3

1-Allyl-6,8-difluoro-1,4-dihydro-4-oxo-7-(1-piperazinyl)quinoline-3-carboxylic acid hydrochloride A mixture of 1-allyl-6,7,8-trifluoro-1,4-dihydro-4-oxo-quinoline-3-carboxylic acid (0.24 g), piperazine (0.37 g), and pyridine (3 ml) was refluxed for 6 hours. After the mixture evaporated to dryness, the residue was adjusted to pH 1 with diluted hydrochloric acid and cooled. The solid was filtered off and recrystallized from water to give 1-allyl-6,8-difluoro-1,4-dihydro-4-oxo-7-(1-piperazinyl) quinoline-3-carboxylic acid hydrochloride (0.12 g), mp 278°–281° C. (decomp.).

|  | C | H | N |
|---|---|---|---|
| Anal. Calcd. for $C_{17}H_{17}F_2N_3O_3HCl$: | 52.93 | 4.70 | 10.89 |
| Found: | 52.65 | 4.68 | 10.82 |

The starting material, 1-allyl-6,7,8-trifluoro-1,4-dihydro-4-oxoquinoline-3-carboxylic acid (mp 194°–197° C.), was obtained by the same method as mentioned for the starting material in Example 1 by using allyl bromide instead of methyl iodide.

EXAMPLE 4

6,8-Difluoro-1-(2-fluoroethyl)-1,4-dihydro-4-oxo-7-(1-piperazinyl)quinoline-3-carboxylic acid hydrochloride To a mixture of 6,7,8-trifluoro-1-(2-fluoroethyl)-1,4-dihydro-4-oxoquinoline-3-carboxylic acid (0.2 g) and piperazine (0.3 g) was added pyridine (5 ml) and the mixture was refluxed for 6 hours. The solvent was evaporated and the residue was strongly acidified with aqueous hydrochloric acid solution. After cooled, the solid was filtered off and recrystallized from water to give 6,8-difluoro-1-(2-fluoroethyl)-1,4-dihydro-4-oxo-7-(1-piperazinyl)-quinoline-3-carboxylic acid hydrochloride (0.09 g), mp 291°–294° C. (decomp.).

|  | C | H | N |
|---|---|---|---|
| Anal. Calcd. for $C_{16}H_{16}F_3N_3O_3HCl$: | 49.05 | 4.37 | 10.73 |
| Found: | 49.04 | 4.36 | 10.68 |

The starting material, 6,7,8-trifluoro-1-(2-fluoroethyl)-1,4-dihydro-4-oxoquinoline-3-carboxylic acid, was prepared by the method described below.

Anhydrous potassium carbonate (2.2 g), 6,7,8-trifluoro-1,4-dihydro-4-oxoquinoline-3-carboxylic acid ethyl ester (0.8 g), 1-bromo-2-fluoroethane (3.8 g), sodium iodide (4.5 g), and DMF (30 ml) were combined and heated with stirring at 90°–100° C. for 10 hours. After the solvent evaporated and cooled, water was added to the residue and extracted with dichloromethane. The organic layer was washed with water, dried over anhydrous sodium sulfate, and evaporated. To the residual solid was added a mixture of 18% hydrochloric acid (14 ml) and ethanol (7 ml) and the acidic mixture was refluxed for 2.5 hours. Water (14 ml) and ethanol (14 ml) were added to the reaction mixture and cooled. The precipitate was collected by filtration and recrystallized from a mixture of DMF and ethanol to give 6,7,8-trifluoro-1-(2-fluoroethyl)-1,4-dihydro-4-oxoquinoline-3-carboxylic acid (0.34 g), mp 208°–210° C.

|  | C | H | N |
|---|---|---|---|
| Anal. Calcd. for $C_{12}H_7F_4NO_3$: | 49.84 | 2.44 | 4.84 |
| Found: | 49.86 | 2.37 | 5.01 |

EXAMPLE 5

6,8-Difluoro-1-(2-fluoroethyl)-1,4-dihydro-7-(4-methyl-1-piperazinyl)-4-oxoquinoline-3-carboxylic acid hydrochloride A mixed solution of 1-methylpiperazine (0.34 g) and pyridine (3 ml) was added to 6,7,8-trifluoro-1-(2-fluoroethyl)-1,4-dihydro-4-oxoquinoline-3-carboxylic acid (0.12 g) and heated to reflux for 6 hours. After the solvent evaporated and cooled, the residue was adjusted to pH 1 with aqueous hydrochloric acid. The cooled mixture was filtered off and the solid recrystallized from water to give 6,8-difluoro-1-(2-fluoroethyl)-1,4-dihydro-7-(4-methyl-1-piperazinyl)-4-oxoquinoline-3-carboxylic acid hydrochloride (0.08 g), mp 269°–271° C. (decomp.).

|   | C | H | N |
|---|---|---|---|
| Anal. Calcd. for C$_{17}$H$_{18}$F$_3$N$_3$O$_3$HCl: | 50.32 | 4.72 | 10.36 |
| Found: | 50.12 | 4.97 | 10.24 |

EXAMPLE 6

7-(4-Allyl-1-piperazinyl)-1-ethyl-6,8-difluoro-1,4-dihydro-4-oxoquinoline-3-carboxylic acid A mixture of 1-ethyl-6,8-difluoro-1,4-dihydro-4-oxo-7-(1-piperazinyl)quinoline-3carboxylic acid hydrochloride (0.18 g), triethylamine (0.12 g), allyl bromide (0.09 g), and DMF (3 ml) was heated with stirring at 90° for 3 hours and the solvent was evaporated. The residue was dissolved in 2N sodium hydroxide solution. The alkaline solution was adjusted to pH 7 with aqueous acetic acid and extracted with dichloromethane. The organic layer was washed with water, dried over anhydrous sodium sulfate, and evaporated. The residue was recrystallized from a mixture of DMF and ethanol to give 7-(4-allyl-1-piperazinyl)-1-ethyl-6,8-difluoro-1,4-dihydro-4-oxoquinoline-3-carboxylic acid (0.055 g), mp 227°–230° C. (decomp.).

|   | C | H | N |
|---|---|---|---|
| Anal. Calcd. for C$_{19}$H$_{21}$F$_2$N$_3$O$_3$ ¼H$_2$O: | 59.76 | 5.67 | 11.00 |
| Found: | 59.69 | 5.52 | 10.89 |

EXAMPLE 7

1-Ethyl-7-(4-ethyl-1-piperazinyl)-6,8-difluoro-1,4-dihydro-4-oxoquinoline-3-carboxylic acid Triethylamine (0.2 g), 1-ethyl-6,8-difluoro-1,4-dihydro-4-oxo-7-(1-piperazinyl)quinoline-3-carboxylic acid hydrochloride (0.3 g), ethyl iodide (0.19 g), and DMF (5 ml) were mixed, heated with stirring at 90° C. for 3 hours, and the solvent was evaporated. The residue was dissolved in 2N sodium hydroxide solution. The alkaline solution was neutralized with aqueous acetic acid and extracted with dichloromethane. The dichloromethane layer was washed with water, dried over anhydrous sodium sulfate, and evaporated. The residue was recrystallized from a mixture of DMF and ethanol to give 1-ethyl-7-(4-ethyl-1-piperazinyl)-6,8-difluoro-1,4-dihydro-4-oxoquinoline-3-carboxylic acid (0.06 g), mp 236°–239° C.

|   | C | H | N |
|---|---|---|---|
| Anal. Calcd. for C$_{18}$H$_{21}$F$_2$N$_3$O$_3$ ¼H$_2$O: | 58.45 | 5.86 | 11.36 |
| Found: | 58.38 | 5.74 | 11.31 |

EXAMPLE 8

1-Ethyl-6,8-difluoro-1,4-dihydro-7-[4-(2-hydroxyethyl)-1-piperazinyl]-4-oxoquinoline-3-carboxylic acid A mixture of 1-ethyl-6,8-difluoro-1,4-dihydro-4-oxo-7-(1-piperazinyl)quinoline-3-carboxylic acid hydrochloride (0.3 g), triethylamine (0.2 g), 2-bromoethanol (0.15 g), and DMF (5 ml) was heated with stirring at 90° C. for 3 hours. After the solvent evaporated, the residue was dissolved in 2N sodium hydroxide solution, neutralized with aqueous acetic acid, and extracted with dichloromethane. The organic layer was washed with water, dried over anhydrous sodium sulfate, and evaporated. The solid was recrystallized from a mixture of DMF and ethanol to give 1-ethyl-6,8-difluoro-1,4-dihydro-7-[4-(2-hydroxyethyl)-1-piperazinyl]-4-oxoquinoline-3-carboxylic acid (0.08 g), mp 225°–228° C.

|   | C | H | N |
|---|---|---|---|
| Anal. Calcd. for C$_{18}$H$_{21}$F$_2$N$_3$O$_4$: | 56.69 | 5.55 | 11.02 |
| Found: | 56.43 | 5.62 | 10.93 |

EXAMPLE 9

1-Ethyl-6,8-difluoro-1,4-dihydro-7-(4-hydroxy-1-piperidinyl)-4-oxoquinoline-3-carboxylic acid To a solution of pyridine (3 ml) and 4-hydroxy-piperidine (1.6 g), 1-ethyl-6,7,8-trifluoro-1,4-dihydro-4-oxoquinoline-3-carboxylic acid (0.43 g) was added and the mixture was heated to reflux for 6 hours. After the solvent evaporated off, the residue was treated with water, acidified wth acetic acid and extracted with dichloro methane. The organic layer was washed with water, dried over anhydrous sodium sulfate, and evaporated. The residue was recrystallized from a mixture of DMF and ethanol to afford 1-ethyl-6,8-difluoro-1,4-dihydro-7-(4-hydroxy-1-piperidinyl-4-oxoquinoline-3-carboxylic acid (0.42 g), mp 216°–218° C.

|   | C | H | N |
|---|---|---|---|
| Anal. Calcd. for C$_{17}$H$_{18}$F$_2$N$_2$O$_4$ ¼H$_2$O: | 57.22 | 5.23 | 7.85 |
| Found: | 57.41 | 5.01 | 8.03 |

EXAMPLE 10

1-Ethyl-6,8-difluoro-1,4-dihydro-7-(3-hydroxy-1-piperidinyl)-4-oxoquinoline-3-carboxylic acid A mixture of 1-ethyl-6,7,8-trifluoro-1,4-dihydro-4-oxo-quinoline-3-carboxylic acid (0.43 g), 3-hydroxypiperidine (1.6 g), and pyridine (3 ml) was refluxed for 6 hours. The mixture was evaporated to dryness, treated with water, acidified with acetic acid, and extracted with dichloromethane. The dichloromethane layer was washed with water, dried over anhydrous sodium sulfate, and evaporated. The residue was recrystallized from a mixture of DMF and ethanol to give 1-ethyl-6,8-difluoro-1,4-dihydro-7-(3-hydroxy-1-piperidinyl)-4-oxoquinoline-3-carboxylic acid (0.3 g), mp 232°–234° C.

|   | C | H | N |
|---|---|---|---|
| Anal. Calcd. for C$_{17}$H$_{18}$F$_2$N$_2$O$_4$ ¼H$_2$O: | 57.22 | 5.23 | 7.85 |
| Found: | 57.18 | 5.13 | 7.97 |

EXAMPLE 11

1-Ethyl-6,8-difluoro-1,4-dihydro-4-oxo-7-(1-pyrrolidinyl)quinoline-3-carboxylic acid A mixture of 1-ethyl-6,7,8-trifluoro-1,4-dihydro-4-oxo-quinoline-3-carboxylic acid (0.43 g), pyrrolidine (1.2 g), and pyridine (3 ml) was refluxed for 6 hours. The solvent was evaporated off. The residue was treated with water, acidified with acetic acid, and extracted with dichloromethane. The organic layer was washed with water, dried over anhydrous sodium sulfate, and evaporated. The solid was recrystallized from a mixture of DMF and ethanol and gave 1-ethyl-6,8-difluoro-1,4-dihydro-4-oxo-7-(1-pyrrolidinyl)quinoline-3-carboxylic acid (0.34 g), mp 284°–286° C. (decomp.).

|  | C | H | N |
|---|---|---|---|
| Anal. Calcd. for $C_{16}H_{16}F_2N_2O_3 \cdot \frac{1}{4}H_2O$: | 58.80 | 5.09 | 8.57 |
| Found: | 58.54 | 4.87 | 8.62 |

EXAMPLE 12

1-Ethyl-6,8-difluoro-1,4-dihydro-7-(4-morpholinyl)4-oxoquinoline-3-carboxylic acid A mixture of 1-ethyl-6,7,8-trifluoro-1,4-dihydro-4-oxoquinoline-3-carboxylic acid (0.43 g), morpholine (1.4 g), and pyridine (3 ml) was refluxed for 6 hours. After the mixture evaporated to dryness, the residue was acidified with aqueous acetic acid and extracted with dichloromethane. The organic layer was washed with water, dried, and evaporated. The solid was recrystallized from a mixture of DMF and ethanol and gave 1-ethyl-6,8-difluoro-1,4-dihydro-7-(4-morpholinyl)-4-oxoquinoline-3-carboxylic acid (0.28 g), mp 268°–271° C. (decomp.).

|  | C | H | N |
|---|---|---|---|
| Anal. Calcd. for $C_{16}H_{16}F_2N_2O_4 \cdot \frac{1}{4}H_2O$: | 56.06 | 4.85 | 8.17 |
| Found: | 56.27 | 4.65 | 8.32 |

EXAMPLE 13

1-Ethyl-6,8-difluoro-1,4-dihydro-7-(4-dimethylamino-1-piperidinyl)-4-oxoquinoline-3-carboxylic acid A mixture of 1-ethyl-6,7,8-trifluoro-1,4-dihydro-4-oxoquinoline-3-carboxylic acid (0.43 g), 4-dimethylaminopiperidine (2.1 g), and pyridine (3 ml) was refluxed for 6 hours. The mixture was evaporated to dryness. The residue was treated with water and extracted with dichloromethane. The organic layer was washed with water, dried, and evaporated. The solid was recrystallized from ethyl acetate and gave 1-ethyl-6,8-difluoro-1,4-dihydro-7-(4-dimethylamino-1-piperidinyl)-4-oxoquinoline-3-carboxylic acid (0.22 g), mp 210°–211° C.

|  | C | H | N |
|---|---|---|---|
| Anal. Calcd. for $C_{19}H_{23}F_2N_3O_3 \cdot \frac{1}{4}H_2O$: | 59.44 | 6.17 | 10.95 |
| Found: | 59.44 | 6.01 | 10.77 |

EXAMPLE 14

6,8-Difluoro-1,4-dihydro-1-(2-hydroxyethyl)-4-oxo-7-(1-piperazinyl)-quinoline-3-carboxylic acid hydrochloride A mixture of 6,7,8-trifluoro-1,4-dihydro-1-(2-hydroxyethyl)-4-oxoquinoline-3-carboxylic acid (0.14 g), piperazine (0.22 g), and pyridine (3 ml) was refluxed for 6hours. After the mixture evaporated to dryness, the residue was strongly acidified with aqueous hydrochloric acid and cooled. The solid was filtered off and recrystallized from water to give 6,8-difluoro-1,4-dihydro-1-(2-hydroxyethyl)-4-oxo-7-(1-piperazinyl) quinoline-3-carboxylic acid hydrochloride (0.05 g), mp 298°–300° C. (decomp.).

|  | C | H | N |
|---|---|---|---|
| Anal. Calcd. for $C_{16}H_{17}F_2N_3O_4 \cdot HCl$: | 49.30 | 4.65 | 10.78 |
| Found: | 48.94 | 4.50 | 10.76 |

The starting material, 6,7,8-trifluoro-1,4-dihydro-1-(2-hydroxyethyl)-4-oxoquinoline-3-carboxylic acid, was prepared as described for the starting material in Example 1 by using 2-bromoethanol instead of methyl iodide.

EXAMPLE 15

6,8-Difluoro-1,4-dihydro-4-oxo-7-(1-piperazinyl)-1-vinylquinoline-3-carboxylic acid hydrochloride To a solution of sodium hydroxide (0.2 g), water (2.5 ml), and ethanol (2.5 ml), 7(4-acetyl-1-piperazinyl)-1-(2-chloroethyl)-6,8-difluoro-1,4-dihydro-4-oxoquinoline-3-carboxylic acid ethyl ester (0.2 g) was added and the mixture was heated with stirring at 80°–90° C. for 3 hours. After cooled, the reaction mixture was strongly acidified with concentrated hydrochloric acid.

The precipitate was filtered off and recrystallized from water to give 6,8-difluoro-1,4-dihydro-4-oxo-7-(1-piperazinyl)-1-vinylquinoline-3-carboxylic acid hydrochloride, mp 267°–270° C. (decomp.); mass spectrum, m/e 335 ($M^+$-HCl).

The starting material, 7-(4acetyl-1-piperazinyl)-1-(2-chloroethyl)-6,8-difluoro-1,4-dihydro-4-oxoquinoline-3-carboxylic acid ethyl ester, was prepared by the following method.

A mixture of 6,7,8-trifluoro-1,4-dihydro-4-oxoquinoline-3-carboxylic acid ethyl ester (4.1 g), anhydrous potassium carbonate (5.2 g), 2-bromoethanol (9.5 g), and DMF (90 ml) was stirred at 100° C. for 10 hours. After the mixture evaporated to dryness, the residue was treated with water, extracted with dichloromethane, washed with water, dried, and evaporated.

The solid was recrystallized from ethanol to give 6,7,8-trifluoro-1,4-dihydro-1-(2-hydroxyethyl)-4-oxoquinoline-3-carboxylic acid ethyl ester (mp 175°–177° C.).

A mixture of the above 1-(2-hydroxyethyl)quinoline ester (1.2 g), piperazine (1.7 g), and pyridine (10 ml) was refluxed for 4 hours. After the mixture evaporated to dryness, the residue was treated with water, made basic with potassium carbonate, and extracted with dichloromethane. The organic layer was washed with water, dried, and evaporated to give 6,8-difluoro-1,4-dihydro-1-(2-hydroxyethyl)-4-oxo-7-(1-piperazinyl)quinoline-3-carboxylic acid ethyl ester.

To a solution of the above 7-(1-piperazinyl) quinoline ester (1.1 g) and acetic acid (6.5 ml), acetic anhydride (0.4 g) was added and the mixture was stirred at 80° C. for 1 hours. After the solvent was evaporated, the residue was treated with water and extracted with dichloromethane. The organic layer was washed with water, dried, and evaporated to give 7-(4-acetyl-1-piperazinyl)-6,8-difluoro-1,4-dihydro-1-(2-hydroxyethyl)-4-oxoquinoline-3-carboxylic acid ethyl ester.

To an ice-cooled solution of the above 7-(4-acetyl-1-piperazinyl)quinoline ester (1.0 g), pyridine (0.27 g), and chloroform (30 ml), a solution of thionylchloride (3.2 g) and chloroform (13 ml) was added dropwise. The mixture was stirred at room temperature for 15 hours. The solvent was evaporated.

The residue was made weakly basic with aqueous potassium carbonate, extracted with chloroform, washed with water, dried, and evaporated. The residue was purified by chromatography on alumina with chloroform as the eluting agent to give 7-(4-acetyl-1-piperazinyl)-1-(2-chloroethyl)-6,8-difluoro-1,4-dihydro-4-oxoquinoline-3-carboxylic acid ethyl ester.

oxoquinoline-3-carboxylic acid silver salt (284 mg), mp 181°–184° C. (decomp.).

Experiment 1 Antibacterial Activity

The antibacterial activities of the compounds of the present invention were assayed by the standard agar dilution streak method against Gram-positive and Gram-negative bacteria [Chemotherapy, 22, 1126 (1974)]. The result was shown in Table 1.

TABLE 1

Antibacterial Activity

| Organisms | Minimum inhibitory concentration (µg/ml) | | | | | | | |
|---|---|---|---|---|---|---|---|---|
| | Ex. 1 | Ex. 2 | Ex. 3 | Ex. 4 | Ex. 5 | Ex. 6 | Ex. 7 | Ex. 8 |
| Bacillus subtilis PCI 219 | 0.39 | 0.20 | 0.39 | 0.39 | 0.10 | 0.10 | 0.10 | 0.10 |
| Staphylococcus aureus 209 p | 3.13 | 1.56 | 3.13 | 3.13 | 0.78 | 0.78 | 0.78 | 0.78 |
| S. aureus Terajima | 3.13 | 3.13 | 3.13 | 3.13 | 0.78 | 0.78 | 0.78 | 0.78 |
| S. epidermidis IID 866 | 3.13 | 3.13 | 3.13 | 1.56 | 0.78 | 0.78 | 0.78 | 0.78 |
| Escherichia coli NIHJ JC-2 | ≦0.05 | ≦0.05 | 0.10 | ≦0.05 | ≦0.05 | 0.10 | ≦0.05 | ≦0.05 |
| E. coli ATCC 10536 | 0.10 | 0.20 | 0.39 | 0.10 | 0.10 | 0.39 | 0.10 | 0.20 |
| Proteus vulgaris 3167 | 0.10 | ≦0.05 | 0.10 | ≦0.05 | ≦0.05 | 0.20 | ≦0.05 | 0.10 |
| P. mirabilis IID 994 | 0.10 | 0.10 | 0.20 | ≦0.05 | ≦0.05 | 0.39 | 0.20 | 0.20 |
| P. morganii IID 602 | 0.20 | 0.39 | 0.39 | 0.20 | 0.10 | 0.78 | 0.39 | 0.78 |
| Klebsiella pneumoniae IFO 3512 | ≦0.05 | 0.10 | 0.10 | ≦0.05 | ≦0.05 | ≦0.05 | ≦0.05 | ≦0.05 |
| Enterobacter cloacae IID 977 | 0.10 | 0.78 | 0.78 | ≦0.05 | 0.10 | 1.56 | 0.39 | 0.39 |
| Citrobacter freundii IID 976 | ≦0.05 | 0.20 | 0.20 | ≦0.05 | ≦0.05 | 0.78 | 0.20 | 0.39 |
| Serratia marcescens IID 618 | 0.10 | 0.39 | 0.39 | 0.39 | 0.10 | 1.56 | 0.39 | 0.78 |
| Shigella sonnei IID 969 | ≦0.05 | 0.10 | 0.10 | ≦0.05 | ≦0.05 | 0.20 | 0.10 | 0.10 |
| Salmonella enteritidis IID 604 | 0.10 | 0.20 | 0.20 | 0.05 | 0.10 | 1.56 | 0.39 | 0.78 |
| Yersinia enterocolitica IID 981 | 0.10 | 0.39 | 0.39 | 0.05 | 0.10 | 0.78 | 0.20 | 0.39 |
| Pseudomonas aeruginosa V-1 | 3.13 | 12.5 | 12.5 | 6.25 | 3.13 | 12.5 | 6.25 | 12.5 |
| P. aeruginosa IFO 12689 | 1.56 | 6.25 | 6.25 | 1.56 | 3.13 | 25 | 6.25 | 12.5 |
| Acinetobacter anitratus IID 876 | 1.56 | 1.56 | 3.13 | 3.13 | 0.39 | 0.78 | 0.39 | 1.56 |
| Alcaligenes faecalis 0104002 | 6.25 | 1.56 | 3.13 | 3.13 | 0.78 | 3.13 | 1.56 | 1.56 |

| Organisms | Minimum inhibitory concentration (µg/ml) | | | | | | |
|---|---|---|---|---|---|---|---|
| | Ex. 9 | Ex. 10 | Ex. 11 | Ex. 12 | Ex. 13 | Ex. 14 | Ex. 16 |
| Bacillus subtilis PCI 219 | ≦0.05 | ≦0.05 | ≦0.05 | ≦0.05 | 0.10 | 3.13 | ≦0.05 |
| Staphylococcus aureus 209 p | 0.20 | 0.20 | 0.10 | 0.20 | 0.39 | 12.5 | 0.20 |
| S. aureus Terajima | 0.20 | 0.39 | 0.10 | 0.39 | 0.39 | 25 | 0.39 |
| S. epidermidis IID 866 | 0.39 | 0.78 | 0.20 | 0.39 | 0.39 | 12.5 | 0.39 |
| Escherichia coli NIHJ JC-2 | 0.20 | 0.39 | 0.20 | 0.20 | ≦0.05 | 0.39 | 0.78 |
| E. coli ATCC 10536 | 0.20 | 0.78 | 0.20 | 0.39 | 0.20 | 0.39 | 0.78 |
| Proteus vulgaris 3167 | ≦0.05 | 0.10 | ≦0.05 | ≦0.05 | 0.10 | 0.39 | 0.10 |
| P. mirabilis IID 994 | | 0.39 | 0.10 | 0.20 | 0.39 | 1.56 | 0.39 |
| P. morganii IID 602 | 0.78 | 1.56 | 0.39 | 0.78 | 1.56 | 1.56 | 1.56 |
| Klebsiella pneumoniae IFO 3512 | ≦0.05 | 0.10 | ≦0.05 | ≦0.05 | ≦0.05 | 0.39 | 0.10 |
| Enterobacter cloacae IID 977 | 1.56 | 6.25 | 1.56 | 1.56 | 3.13 | 0.39 | 3.13 |
| Citrobacter freundii IID 976 | 0.78 | 1.56 | 0.39 | 0.78 | 0.39 | 0.20 | 1.56 |
| Serratia marcescens IID 618 | 1.56 | 3.13 | 1.56 | 1.56 | 0.78 | 6.25 | 3.13 |
| Shigella sonnei IID 969 | 0.20 | 0.78 | 0.20 | 0.20 | 0.10 | 0.20 | 0.39 |
| Salmonella enteritidis IID 604 | 1.56 | 6.25 | 1.56 | 1.56 | 0.78 | 0.39 | 1.56 |
| Yersinia enterocolitica IID 981 | 0.78 | 1.56 | 0.39 | 0.39 | 0.78 | 0.39 | 1.56 |
| Pseudomonas aeruginosa V-1 | 6.25 | 25 | 6.25 | 12.5 | 12.5 | 1.56 | 3.13 |
| P. aeruginosa IFO 12689 | 12.5 | 25 | 6.25 | 12.5 | 25 | 12.5 | 25 |
| Acinetobacter anitratus IID 876 | 1.56 | 1.56 | 0.39 | 1.56 | 0.78 | 25 | 1.56 |
| Alcaligenes faecalis 0104002 | 1.56 | 3.13 | 0.39 | 1.56 | 6.25 | 100 | 3.13 |

EXAMPLE 16

1-Ethyl-6,8-difluoro-1,4-dihydro-7-(4-hydroxy-1-piperidinyl)-4-oxoquinoline-3-carboxylic acid silver salt To a stirred solution of 1-ethyl-6,8-difluoro-1,4-dihydro-7-(4-hydroxy-1-piperidinyl)-4-oxoquinoline-3-carboxylic acid (235 mg), sodium hydroxide (26.7 mg), and water (3 ml), a solution of silver nitrate (113 mg) and water (2 ml) was added. The precipitate was filtered off, washed with water, and dried to give 1-ethyl-6,8-difluoro-1,4-dihydro-7-(4-hydroxy-1-piperidinyl)-4-

What is claimed is:

1. 6,8-Difluoro-1-(2-fluoroethyl)-1,4-dihydro-4-oxo-7-(1-piperazinyl)quinoline-3-carboxylic acid, the hydrates, or the pharmaceutically acceptable salts thereof.

2. 6,8-Difluoro-1-(2-fluoroethyl)-1,4-dihydro-7-(4-methyl-1-piperazinyl)-4-oxoquinoline-3-carboxylic acid, the hydrates, or the pharmaceutically acceptable salts thereof.

3. 6,8-Difluoro-1,4-dihydro-4-oxo-7-(1-piperazinyl)-1-vinylquinoline-3-carboxylic acid, the hydrates, or the pharmaceutically acceptable salts thereof.

* * * * *

UNITED STATES PATENT AND TRADEMARK OFFICE
CERTIFICATE OF CORRECTION

PATENT NO. : B1 4,398,029

DATED : June 5, 1990

INVENTOR(S) : Tsutomu Irikura, Seigo Suzue, Akira Ito, Hiroshi Koga

It is certified that error appears in the above-identified patent and that said Letters Patent is hereby corrected as shown below:

On the title page, under [75] Inventors:, change

>"Tsutomu Irikura, Oizumigakuen
>Hiroshi Koga, Omiya
>Satoshi Murayama, Nogi"

to

>--Tsutomu Irikura, Oizumigakuen
>Seigo Suzue, Saitama-ken
>Akira Ito, Saitama-ken
>Hiroshi Koga, Omiya, all of Japan--

Signed and Sealed this

Fourth Day of February, 1992

*Attest:*

HARRY F. MANBECK, JR.

*Attesting Officer*  *Commissioner of Patents and Trademarks*

REEXAMINATION CERTIFICATE (1298th)
United States Patent [19]

Irikura et al.

[11] B1 4,398,029

[45] Certificate Issued  Jun. 5, 1990

[54] QUINOLINE CARBOXYLIC ACID DERIVATIVES AND PROCESS FOR THE PREPARATION

[75] Inventors: Tsutomu Irikura, Oizumigakuen; Hiroshi Koga, Omiya; Satoshi Murayama, Nogi, all of Japan

[73] Assignee: Kyorin Seiyaku Kabushiki Kaisha, Tokyo, Japan

Reexamination Request:
No. 90/001,739, Mar. 30, 1989

Reexamination Certificate for:
Patent No.: 4,398,029
Issued: Aug. 9, 1983
Appl. No.: 236,168
Filed: Feb. 20, 1981

[51] Int. Cl.$^5$ .................. C07D 401/04; A61K 31/495
[52] U.S. Cl. ......................................... 544/463; 544/4; 544/128; 544/336; 546/5; 546/8; 546/156
[58] Field of Search ......................................... 544/363

[56] References Cited

U.S. PATENT DOCUMENTS

| | | | |
|---|---|---|---|
| 3,849,421 | 11/1974 | Nakagome et al. | 546/123 |
| 4,017,622 | 4/1977 | Minami et al. | 544/363 |
| 4,146,719 | 3/1979 | Irikura | 544/363 |
| 4,448,962 | 5/1984 | Irikura et al. | 544/363 |

FOREIGN PATENT DOCUMENTS

| | | | |
|---|---|---|---|
| 879106 | 10/1979 | Belgium . | |
| 884824 | 12/1980 | Belgium . | |
| 2939786 | 4/1980 | Fed. Rep. of Germany . | |
| 2437406 | 4/1980 | France . | |
| 55-47658 | 4/1980 | Japan . | |
| 56-128764 | 10/1981 | Japan | 544/363 |
| 484578 | 5/1980 | Spain . | |
| 2034698 | 6/1980 | United Kingdom . | |

OTHER PUBLICATIONS

Abstract of paper presented at Annual Meeting of the Pharmaceutical Society of Japan, Apr. 1978, p. 223 (Exhibit 5).

*Primary Examiner*—Glennon H. Hollrah

[57] ABSTRACT

This invention relates to new compounds of value as antibacterial agent. More particularly, it relates to quinoline carboxylic acid derivatives, the hydrates and the salts thereof.

REEXAMINATION CERTIFICATE ISSUED UNDER 35 U.S.C. 307

THE PATENT HAS BEEN AMENDED AS INDICATED BELOW

AS A RESULT OF REEXAMINATION, IT HAS BEEN DETERMINED THAT:

The patentability of claim 2 is confirmed.

Claims 1 and 3 are cancelled.

* * * * *